(12) United States Patent
Chiu et al.

(10) Patent No.: US 6,690,460 B2
(45) Date of Patent: Feb. 10, 2004

(54) REAL TIME DETECTION OF CRACKED QUARTZ WINDOW

(75) Inventors: Te-Chin Chiu, Miaoli (TW); Richard Chen, Jubei (TW); Tsai-Yi Chen, Hsinchu (TW)

(73) Assignee: Taiwan Semiconductor Manufacturing Co., Ltd., Hsin Chu (TW)

( * ) Notice: Subject to any disclaimer, the term of this patent is extended or adjusted under 35 U.S.C. 154(b) by 0 days.

(21) Appl. No.: 10/185,191

(22) Filed: Jun. 27, 2002

(65) Prior Publication Data

US 2004/0001199 A1 Jan. 1, 2004

(51) Int. Cl.$^7$ ............................................. G01N 21/00
(52) U.S. Cl. ............................ 356/239.1; 356/239.2; 250/559.4
(58) Field of Search .................... 356/237.1, 239.1, 356/239.2, 239.3, 239.4, 239.5, 239.6, 239.7, 239.8; 250/339.11, 341.8, 227.95, 259.4

(56) References Cited

U.S. PATENT DOCUMENTS

| | | | | |
|---|---|---|---|---|
| 3,478,218 A | * | 11/1969 | Woellner et al. | 250/559.42 |
| 3,782,827 A | * | 1/1974 | Nisenson et al. | 356/600 |
| 4,213,702 A | * | 7/1980 | Bryant et al. | 356/239.4 |
| 4,597,665 A | * | 7/1986 | Galbraith et al. | 356/239.8 |
| 4,975,670 A | * | 12/1990 | Krinickas, Jr. | 336/60 |
| 5,007,096 A | * | 4/1991 | Yoshida | 382/142 |
| 5,266,806 A | * | 11/1993 | Barber | 250/341.4 |
| 5,459,330 A | * | 10/1995 | Venaille et al. | 250/559.45 |
| 5,570,431 A | * | 10/1996 | Gillard et al. | 382/149 |
| 6,112,013 A | * | 8/2000 | Hsiao et al. | 392/497 |
| 6,285,449 B1 | * | 9/2001 | Ellingson et al. | 356/237.1 |
| 6,404,490 B2 | * | 6/2002 | Blasing | 356/239.8 |
| 6,512,239 B1 | * | 1/2003 | Weiss et al. | 250/559.4 |

* cited by examiner

Primary Examiner—Frank G. Font
Assistant Examiner—Sang H. Nguyen
(74) Attorney, Agent, or Firm—Tung & Associates

(57) ABSTRACT

A method of detecting a crack in a body of a quartz window provides for having a source of a laser beam and a light receiver; applying a reflective coating onto an exterior surface of the quartz window; directing the laser beam from the source into the quartz window so that, in the course of successive reflections of the beam from an exterior surface of the quartz window, the beam undergoes a plurality of predetermined strokes within the body of the quartz window thus probing the body, making the conclusion of the absence of a crack in the body of the quartz window by receiving a reflected beam by the light receiver, which is installed so as to catch the beam having unobtrusively passed through the body of the quartz window, or arriving at the conclusion of the presence of a crack in the body of the quartz window if a reflected beam is not received by the light receiver.

7 Claims, 1 Drawing Sheet

REAL TIME DETECTION OF CRACKED QUARTZ WINDOW

BACKGROUND OF THE INVENTION

1. Field of the Invention

The present invention relates generally to detecting abnormalities in a quartz window, and more particularly to using a laser beam to perform precise real-time monitoring of the quartz window for use with equipment employed in processing wafers.

2. Description of the Related Art.

The semiconductor industry provides chips that run everything from the leading edge computers to the microwaves. The industry has made great technological leaps in the past decade to make chips smaller and faster.

The manufacturing of microchips is performed by a process called lithography. The process revolves around a mask. The shape of a desired chip pattern is written to the mask by electron beams. The mask then becomes the basis for creating thousands of chips. The mask is put in front of a source of light, the light is flashed, and the shadow of the mask is projected onto a silicon wafer. The light that passes through the mask and hits the wafer changes its physical properties. Certain chemicals are used to etch away the parts of the wafer hit by light, not affecting those parts hidden from the light by the mask shadow. In this way, the desired shape of a circuit is transferred from the mask to the wafer. To make a complete chip, a mask with a pattern is flashed, the wafer is etched, another layer of silicon is deposited thereon, a different mask with a different pattern is flashed, and the whole process is repeated many times.

All IC semiconductor products originate from silicon wafers. After being refined, silicon is supplied as amorphous silicon, which means that the atoms are randomly arranged in the material. Under the proper conditions, silicon can be manufactured into epitaxial chunks, which basically means a single crystal. Most gems are examples of single crystals. Diamonds, for example, are merely carbon atoms arranged in a particular 3-D or lattice structure. To manufacture semiconductors, silicon is made use of in a similar lattice form.

Wafers are sliced from a single silicon crystal, which has to be "grown." The growth is performed by melting silicon in a crucible. Pure silicon occurs in two forms—either as a single crystal, or as a collection of atoms with no particular arrangement, called polysilicon. A "seed" or a small silicon crystal is inserted into the crucible holding the molten polysilicon. As the seed is slowly drawn out, the molten silicon aligns with the crystal lattice in the seed. As it cools, the molten silicon expands on this crystal lattice forming an ingot. The entire ingot is drawn out as a single crystal made up of many silicon atoms. This ingot is then sliced into thin wafers, and each wafer is polished to a mirror-like finish. The mirror-like finish of the silicon wafer needs to have a pattern etched into it to make a useful circuit, or circuit element (discrete).

One example of wafer fabrication equipment is the Lam 9600 metal etcher. The Lam Rainbow model 9600 etch system is designed for metal etching of aluminum, aluminum silicon and a limited number of other metals and metal alloys. This is a six-inch tool, but, with some modification to the recipe and wafer transfer, a four-inch wafer can be processed in the system. This system is a single wafer processor and is intended to operate in the automatic mode with cassette-to-cassette wafer transfer. When the system starts operating, all robotic movements are initialized. Then, the transfer arm picks the wafer from the load cassette and transports it to the optical sensor for flat orientation. After the wafer is oriented, it is transported to the entrance load lock and pumped to a suitable transfer pressure. When the proper transfer pressure is reached, the wafer is transported into the chamber for processing. The processing gasses are turned on and stabilized, the RF power is turned on, and the process starts. After the process is complete, the wafer is transported to the exit load lock. This load lock is designed to perform a resist strip and dry surface passivation. The wafer is transported out of the exit (plasma) load lock to a rinse station for wet passivation, spin-dried, and then placed into the exit storage cassette.

One of the above processing steps requires a semiconductor wafer-heating chamber. Between a light source and a wafer, this chamber has an optical element for redistributing the light from the light source. The optical element is constructed in such a manner as to produce the desired illumination (and thus heating) pattern on a semiconductor wafer from the light source. Preferably, the light source is a long-arc lamp mounted above a base plate of a heating chamber. A primary reflector is mounted above the long-arc lamp and is shaped to produce a substantially uniform light distribution on the base plate. A quartz window is mounted between the arc lamp and the base plate. The quartz window acts as a lens to redistribute the light from the lamp and the reflector on the wafer. The window can be constructed as a diffraction grating with a series of lines formed by etching into the window or depositing material on the window to produce a diffraction pattern resulting in the desired illumination pattern on the wafer. Interchangeable quartz windows are used to produce different illumination patterns, which are appropriate for different wafer sizes and different types of heating processes.

A potentially expensive problem arises when the quartz window suffers a crack and all of the wafers that are being processed at the time are ruined and have to be scraped. It is essential to be able to predict in real time when the quartz window is no longer functioning properly so that appropriate actions could be taken to fix the problem.

Prior art methods disclosed the idea of real-time detection utilizing a laser beam. U.S. Pat. No. 5,125,741 issued to Okada et al. discusses a method and apparatus for inspecting surface conditions. This invention concerns inspection of surface conditions to detect locations, sizes and nature of flaws, defects or stains not only on a flat surface but also on an undulating or stepped surface, and includes the steps of scanning an inspected surface of a specimen with a spot-like laser beam projected obliquely from a light source; detecting the height of the inspected surface from a reflected image of the scanning light picked up by a TV camera located above the inspected surface, to maintain the surface at a constant height; converging reflected and diffracted light from the inspected surface toward a photo-detector having measuring points at the point of convergence and at a number of positions along a concentric circle around the point of convergence; measuring the energy of the reflected and diffracted light by photoelectric transducers connected to the respective measuring points; and displaying locations, sizes and nature of surface flaws, defects and stains of the specimen on a monitor, with combined use of the information provided by the picture image of the TV camera as to variations in surface level and cracks on the inspected surface.

Another general approach is shown in U.S. Pat. No. 5,570,431 granted to Gillard et al. for process and apparatus for automatically characterizing, optimizing and checking a crack detection analysis method. It describes a quantitative characterization of a crack detection analysis method achieved by determining the detection sensitivity and background noise produced by the analysis method by suitably processing images obtained from one or more control specimens prepared by the method and subjected to appropriate and optimized conditions of illumination. In addition, the crack detection analysis method is optimized by looking for the parameters, which influence the method, and determining the value thereof, which maximizes detection sensitivity and minimizes background noise.

U.S. Pat. No. 3,782,827 issued to Nisenson et al. describes an optical device for characterizing the surface or other properties of a sample. An optical device is disclosed, which is useful for characterizing the surface topography of an opaque sample and for characterizing other properties of transparent samples. In a reflecting mode, a laser is used to illuminate the surface of a rotating sample. Reflected laser light is focused at a pinhole aperture where its intensity is detected. Useful plots of the power spectrum of the reflected coherent light as a function of frequency are obtained, which characterize the surface topography of the sample. A transmitting embodiment of the device is also described wherein the transparent sample is mounted on the backside of a right-angle prism, which has its hypotenuse side silvered. A laser beam enters the front side of the prism while the prism is rotated about the midpoint of its hypotenuse. As in the reflecting mode, useful plots of the power spectrum of the transmitted, diffracted coherent light as a function of frequency are obtained, which characterize properties of the sample. Processes for characterizing surface properties of opaque samples or other properties of transparent samples are also described.

Another implementation of the real-time detection is discussed in U.S. Pat. No. 4,725,139 issued to Hack et al. for a method and apparatus for detecting defects in transparent materials. A method of detecting defects present at the surface and/or internally in transparent materials, particularly of detecting included foreign bodies or bubbles in glass, is disclosed. The test material is scanned with an electromagnetic radiation of a single wavelength, which is set to the penetration depth in the test material. The intensity reflected by the defects is picked up and analyzed. By this method, only defects located up to a specified depth in the material are detected. Visible light as well as UV- or IR radiation may be applied.

Detection of faults in transparent material using lasers is disclosed in U.S. Pat. 3,652,863 issued to Gaskell et al. where an apparatus for inspecting transparent sheet material for internal defects comprises a laser, a scanning device for scanning the laser beam across the sheet, and a light detector for detecting light scattered by internal defects. An analyzing apparatus is used to analyze signals from the scattered light and thereby identify the nature of the defects. A reference light detector is positioned adjacent the edge of the sheet so that the time interval between detection of the beam by the reference detector and the detection of a defect provides a measure of the position of the defect.

A more specific implementation of the above can be seen in U.S. Pat. No. 4,213,702 granted to Bryant et al. A region of a glass bottle is inspected for flaws or checks by scanning the region with a light beam. The passage of a flaw or check through the beam causes a fluctuation in the intensity of the light beam at two spaced apart locations. At each location, a sensor senses the fluctuation in beam intensity caused by the flaw or check. A difference amplifier generates a difference signal based on the sequential detection of the fluctuation in intensity of the light beam at the two locations. The difference signal is rectified and inverted. The inverted difference signal is rectified and combined with the rectified difference signal to produce a combined signal.

The approach presented also relies on other implementations of the real-time crack detection as in U.S. Pat. No. 6,112,013 issued to Hsiao et al. It discusses a method and an apparatus for detecting the crack of a heater of an acid and rinse bath, the bath being filled with an acid solution, the heater being used to heat the acid solution. The heater is constituted of a hollow quartz tube with one closed end and one open end, the closed end is submerged into acid solution, a part of the quartz tube being exposed in the air. The heated filament is inserted into the open end of the heater toward the closed end of the heater, and a moisture detecting device is attached on the inner side wall of the quartz tube. The detecting device uses chemicals that change color by absorbing moisture, or uses electronic component to detect the humidity. Thus, the variation of moisture in the quartz tube is monitored to acknowledge if there any crack of the quartz tube, to replace the defect quartz tube in order to maintain good wafer yields and reduce loss of wafers.

Another relevant prior art is U.S. Pat. No. 6,155,098, granted to Shapiro et al. for a dew point sensor. The sensor comprises a pressure vessel having an entry port, an exit port, and a temperature controlled plate. A quartz crystal resonator is housed within the pressure vessel and disposed in intimate contact with the temperature-controlled plate. A temperature sensor is disposed to generate signals representative of the quartz crystal resonator temperature. A circuitry is coupled to the quartz crystal resonator and the temperature sensor. The circuitry is configured to control the temperature of the quartz crystal resonator, to measure the frequency of the quartz crystal resonator, and to monitor the temperature signals and the frequency of the quartz crystal resonator when exposed to a flow between the entry port and the exit port so as to calculate a dew point value of the flow.

One more prior art reference worth considering is U.S. Pat. No. 6,285,449 issued to Ellingson et al. for an optical method and apparatus for detection of defects and microstructural changes in ceramics and ceramic coatings. The apparatus detects defects and microstructural changes in hard translucent materials such as ceramic bulk compositions and ceramic coatings after the use under load conditions. A beam from a tunable laser is directed onto a sample under study, and the light reflected by the sample is directed to two detectors, with light scattered with a small scatter angle directed to a first detector and light scattered with a larger scatter angle directed to a second detector for monitoring the scattering surface. The sum and ratio of the two detector outputs respectively provide a gray-scale, or "sum" image, and an indication of the lateral spread of the subsurface scatter, or "ratio" image.

The above two-detector system allows for very high-speed crack detection for on-line, real-time inspection of damage in ceramic components. Statistical image processing using a digital image processing approach allows for the quantitative discrimination of the presence and distribution of small flaws in a sample while improving detection reliability. The tunable laser allows for the penetration of the sample to detect defects from the sample's surface to the laser's maximum depth of penetration. A layered optical fiber directs the incoming laser beam to the sample and transmits each scattered signal to a respective one of the two detectors.

SUMMARY OF THE INVENTION

The principal object of the present invention is to provide a method for crack detection of a quartz window.

The object is attained by a method that provides a source of a light beam and a light receiver, directs the light beam from the source into the quartz window where the beam, in the course of its successive reflections from an exterior surface of the quartz window, undergoes a plurality of predetermined strokes within a body of the quartz window thus probing the body. The conclusion of the absence of a crack in the body of the quartz window is arrived at by receiving a reflected beam by the light receiver, which is installed so as to catch the beam having unobtrusively passed through the body of the quartz window.

To enhance the quality of detecting—by preventing the beam from losing its energy because of scattering through the outer surface of the quartz window—by increasing reflectivity of the outer surface, a reflective coating is applied onto an outer surface of the quartz window.

BRIEF DESCRIPTION OF THE DRAWINGS

The above objects and advantages of the present invention will become more apparent from an ensuing description of a preferred embodiment thereof with reference to the attached drawings, in which.

DETAILED DESCRIPTION OF THE PREFERRED EMBODIMENT

Figure 1:
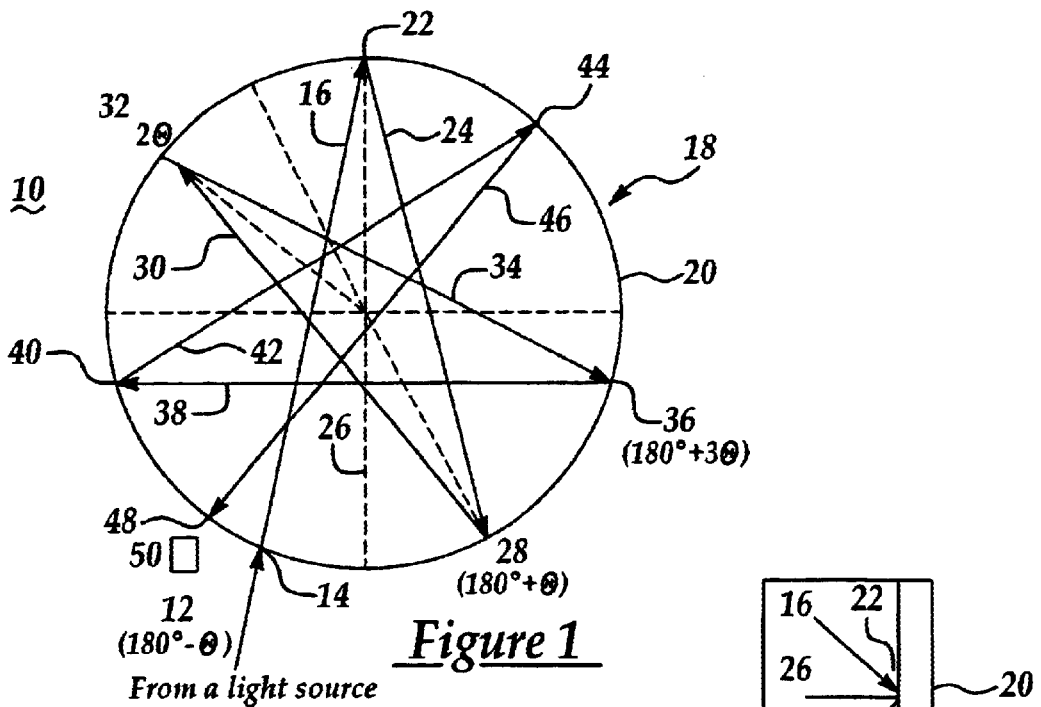
FIG. 1 schematically illustrates a diagram of a beam entering the quartz window (that is not cracked) at a specified location, being reflected inside, and exiting at the expected location.

Referring now to a quartz window 10 in FIG. 1, a beam 12, preferably a laser beam, is introduced into quartz window 10 at an angle of $180°-\theta$, where $180°-\theta$ is an azimuthal coordinate of a point 14 where the beam 12 (shown as 16) falls. To prevent a substantial portion of the falling beam from exiting the quartz window through its outer surface 18, it is suggested that the outer surface 18 of the window 10 be coated with a mirror coating 20, except for the areas of entering the beam and picking it up.

Figure 2:
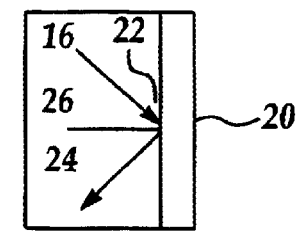
FIG. 2 schematically shows a mirror-coated surface and how it reflects the beam.

The first reflection from a point 22 of the outer surface 18 occurs at angle $\theta$. Based on the optical reflection theory, according to which angles of fall and reflection are equal to each other (see FIG. 2), a reflected laser beam referred to as 24 will arrive at a point, whose coordinate relative to an axis 26 is $180°+\theta$, which is point 28 where the second reflection occurs. If the quartz window 10 is functioning properly and has no cracks, the third reflection (of the beam now designated as 30) occurs at appoint 32 located at $2\theta$. As the laser beam travels onward, the fourth reflection (of beam 34) will happen at a point 36 at $180°+3\theta$. The laser beam continues to be reflected—as beam 38 at a point 40, and further on as beam 42 at point 44, until it exits, as beam 46, the quartz window 10 through point 48 where it is picked up by a receiver 50.

Figure 3:
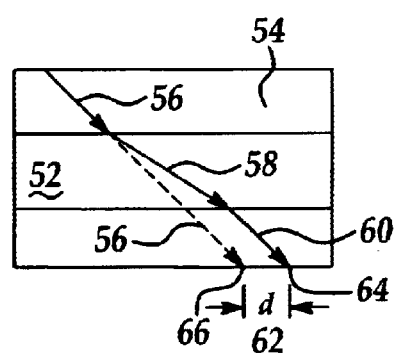
FIG. 3 schematically shows a beam, whose stroke in a quartz body is distorted by a crack.

In any uniform material, light beams travel in straight lines. However, if these beams encounter a boundary between two different materials, they will change direction according to the law of refraction. In our case, if the quartz window 10 is cracked, there will be an air pocket 52 (FIG. 3) formed within a body 54 of the quartz window 10. Since air and quartz have different indices of refraction, the laser beam will no longer be reflected in the same manner as in FIG. 1. Instead of going straight as beam 56, it will refract into 58 and will continue as 60, thus creating a difference 62 of "d" between the actual 64 and expected 66 exit points.

Figure 4:
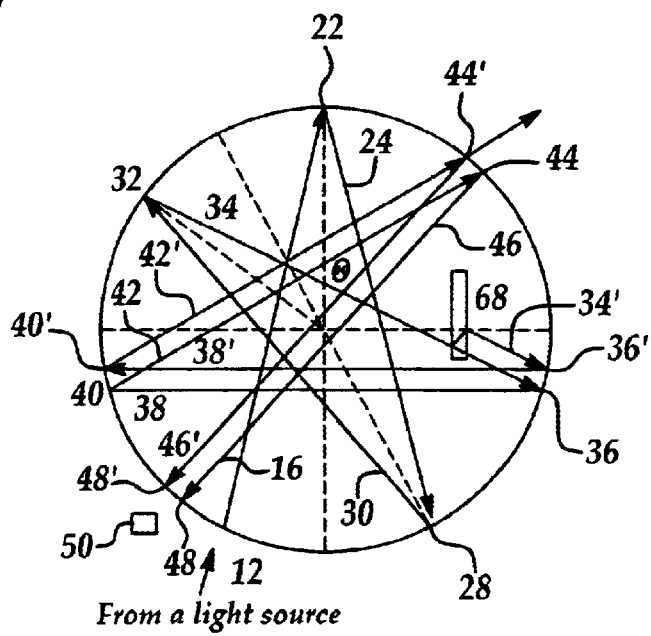
FIG. 4 schematically illustrates a diagram of a beam entering a quartz window at a specified location, being incorrectly reflected inside due to a crack in the quartz window and exiting the quartz window at an unexpected location.

With this in view, FIG. 4 shows that the laser beam 10 follows the trajectory 16–22–24–28–30–32–34 until it confronts a crack 68 in the quartz. In accordance with what was shown in, and discussed in connection with, FIG. 3, the beam will further follow the trajectory 34'–36'–38'–40'–42'–44'–46' and exit at a point 48' where it will be missed by the receiver 50. This event of the beam 12 having been entered into the quartz window 10 and having not been received by the receiver 50 evidences that the quartz window has a crack therein and needs to be replaced.

It is to be understood that the embodiment of the present invention that has been disclosed hereinabove is given by example only and not in a limiting sense. Those skilled in the art may make various modifications and additions to the preferred embodiment chosen to illustrate the invention without departing from the spirit and scope of the present contribution to the art. Accordingly, it is to be realized that the patent protection sought and to be afforded hereby shall be deemed to extend to the subject matter claimed and all equivalence thereof fairly within the scope of the invention.

What is claimed is:

1. A method of detecting a crack in a body of a quartz window comprising the steps of:

providing a source of a light beam and a light receiver;

directing the light beam from the source into the quartz window;

probing the body, said probing being performed by the beam undergoing a plurality of predetermined strokes within the body, said strokes resulting from successive reflections of the beam from an exterior surface of the quartz window; and judging of absence of a crack in the body of the quartz window by receiving a reflected beam by the light receiver, the receiver being installed so as to catch the beam having unobtrusively passed through the body of the quartz window.

2. The method according to claim 1, further including applying a reflective coating onto the exterior surface of the quartz window except for areas thereof used for entering the beam and picking it up.

3. The method according to claim 1, wherein a laser beam is used as the beam.

4. The method according to claim 1, wherein a place where the receiver is installed depends on the number of the reflections selected for the beam, completeness of detecting being higher with increasing the number of the reflections.

5. A method of detecting a crack in a body of a quartz window comprising the steps of:

providing a source of a light beam and a light receiver;

applying a reflective coating onto an exterior surface of the quartz window;

directing the light beam from the source into the quartz window;

probing the body, said probing being performed by the beam undergoing a plurality of predetermined strokes within the body, said strokes resulting from successive reflections of the beam from an exterior surface of the quartz window; and judging of absence of a crack in the body of the quartz window by receiving a reflected beam by the light receiver, the receiver being installed so as to catch the beam having unobtrusively passed through the body of the quartz window.

6. The method according to claim 5, wherein a laser beam is used as the beam.

7. A method of detecting a crack in a body of a quartz window comprising the steps of:

providing a source of a light beam;

directing the light beam from the source into the quartz window;

probing the body, said probing being performed by the beam undergoing a plurality of predetermined strokes within the body, said strokes resulting from successive reflections of the beam from an exterior surface of the quartz window;

providing a light receiver, the receiver being installed so as to catch the light beam having unobtrusively passed through the body of the quartz window, a place where the receiver is installed depending on the number of the reflections selected for the beam, completeness of detecting being higher with increasing the number of the reflections; and judging of absence of a crack in the body of the quartz window by receiving a reflected light beam by the light receiver.

\* \* \* \* \*